US008558006B2

(12) United States Patent
Wang et al.

(10) Patent No.: US 8,558,006 B2
(45) Date of Patent: Oct. 15, 2013

(54) PROCESSES RELATING TO THE ALKYLATION OF PYRAZOLES

(75) Inventors: Linhua Wang, Greensboro, NC (US); Ritesh Bharat Sheth, Greensboro, NC (US); Maren Fuerst, Muenchwilen (CH)

(73) Assignee: Syngenta Crop Protection, LLC, Greensboro, NC (US)

( * ) Notice: Subject to any disclaimer, the term of this patent is extended or adjusted under 35 U.S.C. 154(b) by 0 days.

(21) Appl. No.: 13/387,623

(22) PCT Filed: Jul. 27, 2010

(86) PCT No.: PCT/EP2010/060882
§ 371 (c)(1),
(2), (4) Date: Apr. 27, 2012

(87) PCT Pub. No.: WO2011/012618
PCT Pub. Date: Feb. 3, 2011

(65) Prior Publication Data
US 2012/0203009 A1    Aug. 9, 2012

Related U.S. Application Data

(60) Provisional application No. 61/229,004, filed on Jul. 28, 2009, provisional application No. 61/361,575, filed on Jul. 6, 2010.

(51) Int. Cl.
*C07D 231/14* (2006.01)
*C07D 409/12* (2006.01)

(52) U.S. Cl.
USPC ........................................................ 548/374.1

(58) Field of Classification Search
None
See application file for complete search history.

(56) References Cited

U.S. PATENT DOCUMENTS 5,498,624 A    3/1996    McLoughlin et al.

FOREIGN PATENT DOCUMENTS

| EP | 1 854 788 | 11/2007 |
| WO | 2006/045504 | 5/2006 |
| WO | 2010/009990 | 1/2010 |
| WO | 2011/012620 | 2/2011 |

OTHER PUBLICATIONS

Yamauchi, et al: "Esters of Phosphorus Oxy-acids as Alkylating Agents. Part II", Journal of the Chemical Society, Perkin Transactions 1, Chemical Society, Letchworth; GB, vol. 21, Jan. 1, 1973, pp. 2506-2508.

*Primary Examiner* — Kamal Saeed
(74) *Attorney, Agent, or Firm* — R. Kody Jones (57) ABSTRACT

The present invention relates to processes for the preparation of a compound of formula (I) comprising reacting a compound of formula (IV) with a compound of formula III or (IIIA) in the presence of an acid; wherein $R^1$ is $C_1$-$C_4$ haloalkyl; $R^2$ is optionally substituted alkyl, optionally substituted aryl or optionally substituted heteroaryl; $R^3$ is methyl or ethyl; $R^4$ is hydrogen, optionally substituted alkyl, optionally substituted aryl or optionally substituted heteroaryl; and n is 0 or 1.

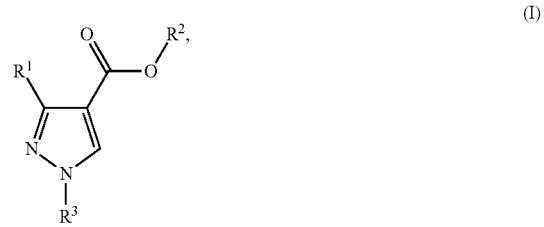

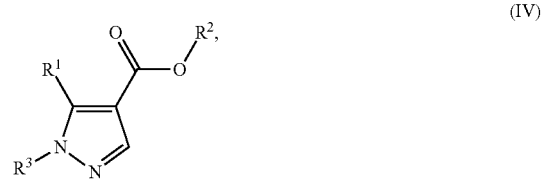

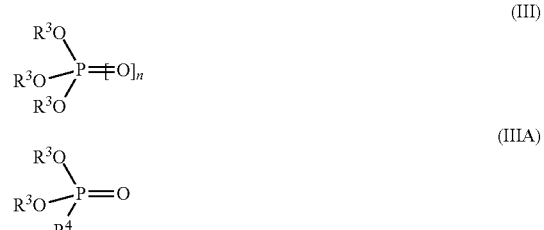

13 Claims, 7 Drawing Sheets

PROCESSES RELATING TO THE ALKYLATION OF PYRAZOLES

This application is a 371 of International Application No. PCT/EP2010/060882 filed Jul. 27, 2010, which claims priority to U.S. 61/229,004 filed Jul. 28, 2009, and U.S. 61/361,575 filed Jul. 6, 2010, the contents of which are incorporated herein by reference.

The present invention relates to N-alkylation of substituted pyrazoles. In particular, the invention relates to the isomerisation of N-alkylated substituted pyrazoles and to the preparation of selected isomers of N-alkylated substituted pyrazoles.

Fungicides for use in crop protection are produced on a very large scale, e.g. thousands of tons per year. Given the scale on which fungicides are produced, any improvement in the production process can represent significant cost savings.

N-alkylated substituted pyrazoles, for example ethyl 3-(difluoromethyl)-1-methyl-1H-pyrazole-4-carboxylate (DFPE), are valuable intermediates in the preparation of a number of fungicides, including Sedaxane, Isopyrazam and others. In DFPE only one of the nitrogen atoms in the pyrazole ring is alkylated.

According to WO 2006/045504, regioselective N-alkylation of substituted pyrazoles may be achieved by reacting the corresponding substituted pyrazoles with trialkyl phosphates or trialkylphosphonates. However, it would be desirable to increase the yield of the non-iso isomer in order to reduce costs and wastage in commercial production. Surprisingly, we have now found that the iso isomer may be rapidly converted into the non-iso isomer by use of an acid.

Accordingly, in a first aspect, the invention provides a process for the preparation of a compound of formula I:

(I)

wherein $R^1$ is $C_1$-$C_4$ haloalkyl;

$R^2$ is optionally substituted alkyl, optionally substituted aryl or optionally substituted heteroaryl; and $R^3$ is methyl or ethyl;

comprising reacting a compound of formula IV:

(IV)

wherein $R^1$, $R^2$ and $R^3$ are as defined for the compound of formula I;

with a compound of formula III or IIIA:

(III)

(IIIA)

wherein n is 0 or 1;

$R^3$ is as defined for the compound of formula I;

$R^4$ is hydrogen, optionally substituted alkyl, optionally substituted aryl or optionally substituted heteroaryl;

in the presence of an acid.

The compound of formula IV is referred to herein as the "iso" isomer with respect to compounds of formula I.

The alkyl groups appearing in the above substituent definitions may be straight-chain or branched and are, for example, methyl, ethyl, n-propyl, isopropyl, n-butyl, sec-butyl, isobutyl or tert-butyl, preferably methyl or ethyl. Halogen is generally fluorine, chlorine, bromine or iodine, preferably fluorine. $C_1$-$C_4$ haloalkyl groups are derived from the mentioned $C_1$-$C_4$ alkyl groups and are preferably difluoromethyl or trifluoromethyl.

Aryl refers to aromatic hydrocarbon ring systems which may be a single ring or multiple rings which are fused together or linked covalently. Examples for aryl groups are phenyl, naphthyl, tetrahydronaphthyl, indanyl, indenyl, anthracenyl, phenanthrenyl and biphenyl.

Heteroaryl refers to aromatic ring systems comprising mono-, bi- or tricyclic systems wherein at least one oxygen, nitrogen or sulfur atom is present as a ring member. Examples are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl and naphthyridinyl.

$R^2$ and $R^4$ for example may be optionally substituted alkyl, optionally substituted aryl or optionally substituted heteroaryl. This means that the alkyl, aryl and heteroaryl groups may or may not carry one or more identical or different substituents. Normally not more than three substituents are present at the same time. Examples of substituents are: halogen, alkyl, haloalkyl, cycloalkyl, cycloalkylalkyl, alkenyl, haloalkenyl, cycloalkenyl, alkynyl, haloalkynyl, alkoxy, haloalkoxy, cycloalkoxy, alkenyloxy, haloalkenyloxy, alkynyloxy, haloalkenyloxy, alkylthio, haloalkylthio, cycloalkylthio, alkenylthio, alkynylthio, alkylcarbonyl, haloalkylcarbonyl, cycloalkylcarbonyl, alkenylcarbonyl, alkynylcarbonyl, alkoxyalkyl, cyano, nitro, hydroxy, mercapto, amino, alkylamino and dialkylamino.

Preferred optional substituents are $C_1$-$C_8$ alkyl, halo-$C_1$-$C_8$ alkyl, $C_3$-$C_8$ cycloalkyl, $C_3$-$C_8$ cycloalkyl-$C_1$-$C_8$ alkyl, $C_2$-$C_8$ alkenyl, halo-$C_2$-$C_8$ alkenyl, $C_3$-$C_8$ cyclo-$C_2$-$C_8$ alkenyl, $C_2$-$C_8$ alkynyl, halo-$C_2$-$C_8$ alkynyl, $C_1$-$C_8$ alkoxy, halo-$C_1$-$C_8$ alkoxy, $C_3$-$C_8$ cycloalkoxy, $C_2$-$C_8$ alkenyloxy, halo-$C_2$-$C_8$ alkenyloxy, $C_2$-$C_8$ alkynyloxy, halo-$C_2$-$C_8$ alkenyloxy, $C_1$-$C_8$ alkylthio, halo-$C_1$-$C_8$ alkylthio, $C_3$-$C_8$ cycloalkylthio, $C_2$-$C_8$ alkenylthio, $C_2$-$C_8$ alkynylthio, $C_1$-$C_8$ alkylcarbonyl, halo- $C_1$-$C_8$ alkylcarbonyl, $C_3$-$C_8$ cycloalkylcarbonyl, $C_2$-$C_8$ alkenylcarbonyl, $C_2$-$C_8$ alkynylcarbonyl, $C_1$-$C_8$ alkoxy-$C_1$-$C_8$ alkyl, cyano, nitro, hydroxy, mercapto, amino, $C_1$-$C_8$ alkylamino and $C_1$-$C_8$ dialkylamino.

More preferred optional substituents are $C_1$-$C_4$ alkyl, halo-$C_1$-$C_4$ alkyl, $C_3$-$C_6$ cycloalkyl, $C_3$-$C_6$ cycloalkyl-$C_1$-$C_4$ alkyl, $C_2$-$C_4$ alkenyl, halo-$C_2$-$C_4$ alkenyl, $C_3$-$C_6$ cyclo-$C_2$-$C_4$ alkenyl, $C_2$-$C_4$ alkynyl, halo-$C_2$-$C_4$ alkynyl, $C_1$-$C_4$ alkoxy, halo-$C_1$-$C_4$ alkoxy, $C_3$-$C_6$ cycloalkoxy, $C_2$-$C_4$ alkenyloxy, halo-$C_2$-$C_4$ alkenyloxy, $C_2$-$C_4$ alkynyloxy, halo-$C_2$-$C_4$ alkenyloxy, $C_1$-$C_4$ alkylthio, halo-$C_1$-$C_4$ alkylthio, $C_3$-$C_6$ cycloalkylthio, $C_2$-$C_4$ alkenylthio, $C_2$-$C_4$ alkynylthio, $C_1$-$C_4$ alkylcarbonyl, halo-$C_1$-$C_4$ alkylcarbonyl, $C_3$-$C_6$ cycloalkylcarbonyl, $C_2$-$C_4$ alkenylcarbonyl, $C_2$-$C_4$ alkynylcarbonyl, $C_1$-$C_4$ alkoxy-$C_1$-$C_4$ alkyl, cyano, nitro, hydroxy, mercapto, amino, $C_1$-$C_4$ alkylamino and $C_1$-$C_4$ dialkylamino.

More preferred optionally substituents are $C_1$-$C_4$ alkyl, $C_1$-$C_4$ haloalkyl, $C_1$-$C_4$ alkoxy, halo-$C_1$-$C_4$ alkoxy, halogen, hydroxy, cyano, nitro and amino.

Typical examples for optionally substituted aryl include 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-methylphenyl, 3-methylphenyl, 4-methylphenyl, 2-methoxyphenyl, 3-methoxyphenyl, 4-methoxyphenyl, 2-cyanophenyl, 3-cyanophenyl, 4-cyanophenyl, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 2,3-difluorophenyl, 2,4-difluorophenyl, 2,5-difluorophenyl, 2,6-difluorophenyl, 3,4-difluorophenyl, 3,5-difluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3-dibromophenyl, 2,4-dibromophenyl, 2,5-dibromophenyl, 2,6-dibromophenyl, 3,4-dibromophenyl, 3,5-dibromophenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3-dicyanophenyl, 2,4-dicyanophenyl, 2,5-dicyanophenyl, 2,6-dicyanophenyl, 3,4-dicyanophenyl, 3,5-dicyanophenyl, 2,3-bis(trifluoromethyl)phenyl, 2,4-bis(trifluoromethyl)phenyl, 2,5-bis(trifluoromethyl)phenyl, 2,6-bis(trifluoromethyl)phenyl, 3,4-bis(trifluoromethyl)phenyl, 3,5-bis(trifluoromethyl)phenyl, 2,3-bis(trifluoromethoxy)phenyl, 2,4-bis(trifluoromethoxy)phenyl, 2,5-bis(trifluoromethoxy)phenyl, 2,6-bis(trifluoromethoxy)phenyl, 3,4-bis(trifluoromethoxy)phenyl, 3,5-bis(trifluoromethoxy)phenyl, 2-chloro-5-fluorophenyl, 2-fluoro-5-methylphenyl, 2-fluoro-5-methoxyphenyl, 5-chloro-2-fluorophenyl, 2-chloro-5-methylphenyl, 2-chloro-5-methoxyphenyl, 5-fluoro-2-methylphenyl, 5-chloro-2-methylphenyl, 5-methoxy-2-methylphenyl, 5-fluoro-2-methoxyphenyl, 5-chloro-2-methoxyphenyl and 2-methoxy-5-methylphenyl.

Typical examples for optionally substituted heteroaryl include 5-methyl-3-trifluoromethylpyrazol-1-yl, 3-methyl-5-trifluoromethylpyrazol-1-yl, 3,5-bis-trifluoromethylpyrazol-1-yl, 3,5-dimethylpyrazol-1-yl, 5-ethyl-3-trifluoromethylpyrazol-1-yl, 5-methyl-3-trifluoromethoxypyrazol-1-yl, 2-methyl-4-trifluoromethylimidazol-1-yl, 4-methyl-2-trifluoromethylimidazol-1-yl, 2,4-bis-trifluoromethylimidazol-1-yl, 2,4-dimethylimidazol-1-yl, 2-ethyl-4-trifluoromethylimidazol-1-yl, 2-methyl-4-trifluoromethoxyimidazol-1-yl, 5-methyl-3-trifluoromethyl[1,2,4]triazol-1-yl, 3-methyl-5-trifluoromethyl[1,2,4]triazol-1-yl, 3,5-bis-trifluoromethyl[1,2,4]triazol-1-yl and 3,5-dimethyl[1,2,4]triazol-1-yl, 5-ethyl-3-trifluoromethyl[1,2,4]triazol-1-yl, 5-methyl-3-trifluoromethoxy[1,2,4]triazol-1-yl.

Cycloalkyl on its own or as part of another substituent is, depending upon the number of carbon atoms mentioned, for example, cyclopropyl, cyclobutyl, cyclopentyl or cyclohexyl.

Alkoxy on its own or as part of another substituent is, depending upon the number of carbon atoms mentioned, for example methoxy, ethoxy, 1-propoxy, 2-propoxy, n-butoxy, 2-n-butoxy, or 2-tert-butoxy.

Alkenyl on its own or as part of another substituent is, depending upon the number of carbon atoms mentioned, for example, ethenyl, allyl, propen-1-yl, buten-2-yl, buten-3-yl, penten-1-yl, penten-3-yl, hexen-1-yl or 4-methyl-penten-3-yl.

Alkynyl on its own or as part of another substituent is, depending upon the number of carbon atoms mentioned, for example, ethynyl, propyn-1-yl, propyn-2-yl, butyn-1-yl, butyn-2-yl, 1-methyl-2-butynyl, hexyn-1-yl or 1-ethyl-2-butynyl.

Preferably n is 1.

Preferably, $R^1$ is difluoromethyl or trifluoromethyl;

Preferably $R^2$ is $C_1$-$C_8$ alkyl, phenyl, or phenyl-$C_1$-$C_8$ alkyl, wherein the alkyl, phenyl and phenylalkyl are each optionally substituted with one or more of, e.g. 1 to 3, $C_1$-$C_4$ alkyl, $C_1$-$C_4$ haloalkyl, $C_1$-$C_4$ alkoxy, halo-$C_1$-$C_4$ alkoxy, halogen, hydroxy, cyano, nitro and amino. More preferably $R^2$ is $C_1$-$C_8$ alkyl or $C_1$-$C_8$ haloalkyl, phenyl or benzyl, wherein the phenyl and benzyl are each optionally substituted with halogen, e.g. 1 to 3 halogen atoms. More preferably $R^2$ is $C_1$-$C_6$ alkyl. Even more preferably $R^2$ is $C_1$-$C_4$ alkyl. Most preferably $R^2$ is methyl or ethyl.

Preferably $R^3$ is methyl.

Preferably $R^4$ is hydrogen, $C_1$-$C_8$ alkyl, phenyl, or phenyl-$C_1$-$C_8$ alkyl, wherein the alkyl, phenyl and phenylalkyl are each optionally substituted with one or more of, e.g. 1 to 3, $C_1$-$C_4$ alkyl, $C_1$-$C_4$ haloalkyl, $C_1$-$C_4$ alkoxy, halo-$C_1$-$C_4$ alkoxy, halogen, hydroxy, cyano, nitro and amino. More preferably $R^4$ is hydrogen, $C_1$-$C_8$ alkyl or $C_1$-$C_8$ haloalkyl, phenyl or benzyl, wherein the phenyl and benzyl are each optionally substituted with halogen. More preferably $R^4$ is hydrogen or $C_1$-$C_6$ alkyl. Most preferably $R^4$ is hydrogen, methyl or ethyl.

The processes according to the invention are suitable preferably for the preparation of compounds of formula I wherein $R^1$ is difluoromethyl or trifluoromethyl; $R^2$ is $C_1$-$C_6$ alkyl, e.g. ethyl; $R^3$ is methyl; and $R^4$ is hydrogen or $C_1$-$C_6$ alkyl, e.g. methyl or ethyl.

The processes according to the invention are especially suitable for the preparation of compounds of formula I wherein $R^1$ is difluoromethyl.

The processes according to the invention are very especially suitable for the preparation of compounds of formula I wherein $R^1$ is difluoromethyl, $R^2$ is ethyl, $R^3$ is methyl and $R^4$ is hydrogen or $C_1$-$C_6$ alkyl.

The processes according to the invention are also very especially suitable for the preparation of compounds of formula I wherein $R^1$ is trifluoromethyl; $R^2$ is ethyl, $R^3$ is methyl and $R^4$ is hydrogen or $C_1$-$C_6$ alkyl.

In preferred processes, the process utilises a compound of formula III in which n is 1. In especially preferred processes, n is 1 and $R^3$ is methyl.

In any aspect of the invention, preferably the compound of formula III or IIIA is dimethyl methyl phosphonate, trimethyl phosphite, trimethyl phosphate or dimethyl phosphate, more preferably trimethyl phosphate.

For example, the invention provides a process for the preparation of a compound of formula I comprising isomerising a compound of formula IV using a compound of formula III or IIIA and an acid.

The acid may be exogenous acid. For example, the acid may be one that is added to the reaction, e.g. as opposed to any acid that may have been formed in situ by the reactions of the invention or by any other reaction. For example, the acid may not be acid formed in situ by a preceding reaction step in which the pyrazaole moiety is alkylated. In another embodiment the acid is one that is not formed in situ from a compound of formula III or IIIA, e.g. it is not an acid formed from a preceding reaction step in which the pyrazole moiety (e.g. a compound of formula II) is alkylated by a compound of formula III or IIIA. Generally, the acid may be an exogenous acid and/or an acid that is not formed in situ from a compound of formula III or IIIA with reference to any aspect of the invention.

The compound of formula IV may provided as a mixture comprising the compound of formula IV and the compound of formula I. For example, compounds of formula IV may be produced by N alkylating the corresponding pyrazole. This will generally result in a mixture of compounds of formula IV and formula I. According to the invention, the proportion of the compound of formula I in the mixture may be improved, e.g. increased, by the addition of acid. Thus the present invention provides a process for increasing the proportion of the compound of formula I in a mixture comprising a compound of formula I and a compound of formula IV.

The compound of formula IV may be provided as a mixture comprising a compound of formula I and a compound of formula IV, and wherein said mixture is prepared by N-alkylating a compound of formula II:

(II)

wherein $R^1$ and $R^2$ are as defined for the compound of formula I;

e.g. thereby producing a mixture comprising a compound of formula I and a compound of formula IV. The mixture may then be reacted with a compound of formula III or IIIA in the presence of an acid.

It may be advantageous in some cases to N alkylate the corresponding substituted pyrazole and isomerise any compound of formula IV produced from the alkylation substantially at the same time, e.g. simultaneously. This may be performed in one step.

Accordingly, in a further aspect, the invention provides a process, e.g. a regioselective process, for the preparation of a compound of formula I:

(I)

wherein $R^1$ is $C_1$-$C_4$ haloalkyl;

$R^2$ is optionally substituted alkyl, optionally substituted aryl or optionally substituted heteroaryl;

$R^3$ is methyl or ethyl;

comprising reacting a compound of formula II:

(II)

wherein $R^1$ and $R^2$ are as defined for the compound of formula I;

with a compound of formula III or IIIA:

(III)

(IIIA)

wherein n is 0 or 1;

$R^3$ is as defined for the compound of formula I; and $R^4$ is hydrogen, optionally substituted alkyl, optionally substituted aryl or optionally substituted heteroaryl;

in the presence of an acid, e.g. an exogenous acid and/or an acid that is other than one formed in situ from a compound of formula III or IIIA.

Preferred definitions of n, $R^1$, $R^2$, $R^3$ and $R^4$ are the same as those given above. Most preferably $R^1$ is difluoromethyl, $R^2$ is $C_1$-$C_6$ alkyl e.g. ethyl and $R^3$ is methyl.

Without being bound by theory, it is thought that the acid acts as a catalyst to inter-convert the compound of formula I and the compound of formula IV, thereby promoting the proportions of the compounds of formula I and IV to thermodynamic equilibrium.

In a further aspect, the invention provides a process for inter-converting a compound of formula IV and a compound of formula I according to Scheme I:

Scheme I wherein $R^1$ is $C_1$-$C_4$ haloalkyl;
$R^2$ is optionally substituted alkyl, optionally substituted aryl or optionally substituted heteroaryl; and
$R^3$ is methyl or ethyl;
using a compound of formula III or IIIA:

wherein n is 0 or 1; $R^3$ is as defined for the compound of formula I and IV; and
$R^4$ is hydrogen, optionally substituted alkyl, optionally substituted aryl or optionally substituted heteroaryl;
and an acid as inter-conversion reagents.

Preferred definitions of n, $R^1$, $R^2$, $R^3$, and $R^4$ are the same as those given above. Most preferably $R^1$ is difluoromethyl, $R^2$ is $C_1$-$C_6$ alkyl, e.g. ethyl, $R^3$ is methyl and $R^4$ is hydrogen or $C_1$-$C_6$ alkyl.

We have found that a wide range of acids catalyse the conversion of compounds of formula IV to compounds of formula I, including mineral acids, Bronsted acids and Lewis acids. Preferably the acid is a Bronsted acid. Suitable acids include organic acids. An organic acid is, for example, an acid that contains a carboxyl group. In particular the acid may be any acid capable of acting as a Bronsted and/or Lewis acid in an organic polar or non-polar solvent. The acid can be a free acid or bound to a solid support, e.g. in a resin or polymer. Without being bound by theory, it is thought that the acid develops positive charge on the oxygen atom of phosphorus-based methylating agent, thereby making the reagent more electrophilic, which in turn catalyses movement of the proportions of the compounds of formula I and IV to thermodynamic equilibrium.

Examples of suitable acids include sulphonic acids, phosphoric acids, phosphonic acids, boron containing compounds, e.g. boronic acids, boranes, haloborons, titanium IV salts, silicon oxides and aluminium oxides. Preferably, the acid is selected from the group consisting of: $MeSO_3H$, polyphosphoric acid, p-Tosyl-OH, orthophosphoric acid, $BF_3$-DMS, $BF_3$-THF, and $Ti(O\text{-isopropyl})_4$. The acid may be tethered to a solid support, e.g. an ion exchange resin. An example is Amberlyst® 15 which is an ion exchange resin with a sulfonic acid functionality.

More preferably the acid is a phosphoric acid, a phosphonic acid or a sulphonic acid, e.g. polyphosphoric acid or $MeSO_3H$. Polyphosphoric acids effectively comprise two or more units of orthophosphoric acid and have an alternating oxygen-phosphor backbone. A general formula for polyphosphoric acid compounds is $HO(PO_2OH)_xH$, where x=number of phosphoric units in the molecule. For example, x may be 1 to 1000, but the invention is not limited by the value of x. Sulphonic acids such as $MeSO_3H$ are particularly preferred.

For the avoidance of doubt, the term phosphoric acid includes orthophosphoric acid ($H_3PO_4$) and polyphosphoric acids. The term sulphonic acid refers to compounds of the formula $R$—$SO^3H$ in which R is an organic radical such as alkyl or phenyl.

The reaction according to the invention can be carried out in an inert solvent, preferably an anhydrous inert solvent. Suitable solvents are, for example, xylene, mesitylene, tert-butyl benzene, chlorobenzene, 1,2-dichlorobenzene, decalin, dibutyl ether, dipentyl ether, diphenyl ether and anisole. The reaction according to the invention is preferably carried out neat, e.g. without an additional solvent.

We have found that increasing the concentration of acid increases the speed at which inter-conversion takes place, however too much acid can result in reduced yield. For example, the acid may be present in the reaction at amounts of 0.1 wt % to 20% wt %, e.g. 0.5 wt % to 10 wt %, e.g. 1 wt % to 6 wt %. The acid may be used such that it is present in the reaction at a concentration of at least 0.1 wt %, at least 0.5 wt %, e.g. at least 1 wt %. Wt % is with respect to the amount of the compound of formula IV, or the combined amount of the compound of formula IV and I when both are present.

For example the acid may be used in an amount 0.01 mol % to 0.5 mol %, preferably 0.02 mol % to 0.1 mol % compared to the molar amount of the compound of formula IV, or the combined molar amount of the compound of formula IV and I when both are present. The amount of acid may be at least 0.01 mol %, preferably at least 0.02 mol % and may be 0.5 mol % or less, preferably 0.1 mol % or less compared to the molar amount of the compound of formula IV, or the combined molar amount of the compound of formula IV and I when both are present. The acid may be used in a catalytic amount.

The temperature of the reaction in which the compound of formula IV is converted into the compound of formula I may be carried out at a temperature of e.g. 50 to 250° C., e.g. 100 to 200° C., e.g. 140 to 180° C. Preferably the reaction is performed at least 100° C., at least 120° C., at least 140° C., at least 160° C. A person skilled in the art would be able to optimise the reaction to find the most suitable temperature.

In the reactions according to the invention, compounds of formula III or IIIA are used e.g. at least at about 0.01 mol % relative to the molar amount of the compound of formula IV, or the molar amount of the compound of formula IV and I when both are present, up to molar excess relative to compounds of formula I and IV, e.g. up to 30-fold excess, e.g. up to 10-fold excess.

Preferably the compound of formula III or IIIA is used at less than an equimolar amount compared to the molar amount of the compound of formula IV, or the combined molar amount of the compound of formula IV and I when both are present, more preferably less than 0.5 mol %, even more preferably less than 0.3 mol %. The amount of compound of formula III or IIIA is preferably at least 0.01 mol %, preferably at least 0.05 mol % compared to the molar amount of the compound of formula IV, or the combined molar amount of the compound of formula IV and I when both are present. The amount of compound of formula III or IIIA is preferably in the range 0.01 mol % to 3 mol %, preferably in the range 0.05 to 0.9 mol %, even more preferably in the range 0.05 mol % to 0.3 mol % compared to the molar amount of the compound of formula IV, or the combined molar amount of the compound of formula IV and I where both are present, Isomerising compounds of formula IV may employ compounds of formula III or IIIA in a catalytic amount.

WO 2008/145257 describes synthesis routes to N-alkylated substituted pyrazoles using methylhydrazine. The use of methylhydrazine instead of hydrazine allows synthesis of N-alkylated substituted pyrazoles in which a methyl group is placed on the desired pyrazole nitrogen atom thereby avoiding the need for a separate step for alkylation. The present invention now provides an alkylation step that allows synthesis of the non-iso isomers with high regioselectivity. This makes a route involving hydrazine more feasible.

In a further aspect, the invention provides a process, e.g. a regioselective process, for the preparation of a compound of formula I:

wherein $R^1$ is $C_1$-$C_4$ haloalkyl;
$R^2$ is optionally substituted alkyl, optionally substituted aryl or optionally substituted heteroaryl; and
$R^3$ is methyl or ethyl;
comprising
a. reacting a compound of formula V:

wherein $R^1$ is $C_1$-$C_4$ haloalkyl; and
$R^2$ is optionally substituted alkyl, optionally substituted aryl or optionally substituted heteroaryl;
$R^5$ is hydrogen, optionally substituted alkyl, optionally substituted aryl or optionally substituted heteroaryl;
with hydrazine to produce a compound of formula II:

wherein $R^1$ and $R^2$ are as defined for formula I; and b. reacting the compound of formula II with a compound of formula III or IIIA:

wherein $R^3$ is as defined for formula I;
n is 0 or 1; and
$R^4$ is hydrogen, optionally substituted $C_1$-$C_6$ alkyl, optionally substituted aryl or optionally substituted heteroaryl;
in the presence of an acid, e.g. an exogenous acid and/or an acid that is other than one formed in situ from a compound of formula III or IIIA.

Preferred definitions of n, $R^1$, $R^2$, $R^3$, $R^4$ are the same as those given above, with the preferred definitions of $R^5$ being the same as for $R^4$. Most preferably $R^1$ is difluoromethyl, $R^2$ is $C_1$-$C_6$ alkyl e.g. ethyl, $R^3$ is methyl, $R^4$ and $R^5$ are independently hydrogen or $C_1$-$C_6$ alkyl, e.g. ethyl.

The compounds of formula II are known or can be prepared using hydrazine analogously to processes known in the literature. For example, such compounds can be prepared from the 3-oxo-carboxylic acid esters on which they are based by means of a two-step synthesis by reaction with trimethyl orthoformate and subsequent reaction with hydrazine. Such reactions are described, for example, in JP-2000-044541. A further synthesis route for the preparation of compounds of formula II is described in JP-2001-322983, wherein, for example, 3-trifluoromethyl-1H-pyrazole-4-carboxylic acid ethyl ester is prepared starting from 3-chloro-4,4,4-trifluoro-2-formyl-2-butenoic acid ethyl ester by reaction with hydrazine. Also, WO 2006/045504 discusses procedures that may be employed for producing compounds of formula II from compounds of formula V using hydrazine. Compounds of formula III and IIIA are commercially available.

The N-alkylation of unsubstituted nitrogen-containing heterocycles is described in Journal of the Chemical Society, Perkin Transactions 1, 21, 2506-2508 (1973) and in Bulletin of the Chemical Society of Japan, 50, 1510-1512 (1977). There is no mention of such alkylating agents having regioselective properties in the N-alkylation of pyrazoles.

In some cases a mixture of compounds of formula III and compounds of formula IIIA may be used. Where a compound of formula III or IIIA is mentioned, this includes mixtures of compounds of formula III and IIIA. Likewise mixtures of different acids may be used.

In a further aspect of the invention, there is provided use of a phosphoric acid, a phosphonic acid, or a sulphonic acid in the conversion of a compound of formula IV:

wherein
R¹ is $C_1$-$C_4$haloalkyl,
R² is optionally substituted alkyl, optionally substituted aryl or optionally substituted heteroaryl; and
R³ is methyl or ethyl;
into a compound of formula I:

(I)

wherein R¹, R² and R³ are as defined for the compound of formula IV.

Preferred definitions of R¹, R², and R³ are the same as those given above. Most preferably R¹ is difluoromethyl, R² is $C_1$-$C_6$ alkyl e.g. ethyl and R³ is methyl.

In a further aspect of the invention there is provided a method, e.g. a regioselective method, of preparing a compound of formula VI:

(VI)

comprising reacting a compound of formula VII:

(VII)

with a compound of formula VIII:

(VIII)

in the presence of a phosphoric acid, a phosphonic acid, or a sulphonic acid.

Compounds of formula I may be subsequently converted into the corresponding acid. Such compounds may also be useful intermediates in the production of fungicides, see e.g. WO 2008/145257. For example, compounds of formula I may be converted into compounds of formula IX:

(IX)

wherein R¹ and R³ are as defined for the compound of formula I;
by hydrolysing the compound of formula I.

Accordingly, the invention provides a process for the preparation of a compound of formula IX:

(IX)

wherein R¹ is $C_1$-$C_4$haloalkyl, and
R³ is methyl or ethyl;
comprising
a. preparing a compound of formula I:

(I)

wherein R¹ and R³ are as defined for the compound of formula I; and
R² is optionally substituted alkyl, optionally substituted aryl or optionally substituted heteroaryl;
according to the invention; and
b. hydrolysing the compound of formula I to produce the compound of formula IX.

Preferred definitions of R¹, R², and R³ are the same as those given above. Most preferably R¹ is difluoromethyl, R² is $C_1$-$C_6$ alkyl e.g. ethyl and R³ is methyl.

Hydrolysis of the compound of formula I may be achieved by performing the steps:
i) saponifying that compound in situ leading to the formation of a compound of formula IX by
ii) adding a base to form the anion of the compound of formula IX;
ii') adding an acid to form the compound of formula IX;
e.g. as described in WO 2008/145257.

In a further aspect the invention provides a process for the preparation of a compound of formula X:

(X)

wherein $R^1$ is $C_1$-$C_4$haloalkyl;
$R^3$ is methyl or ethyl;
A is thienyl, phenyl, or ethylene each optionally substituted by one to three groups independently selected from halogen, methyl and methoxy;
B is a direct bond, cyclopropylene, an annelated bicyclo[2.2.1]heptane- or bicyclo[2.2.1]heptene ring;
D is hydrogen, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_1$-$C_6$ alkylidene, $C_1$-$C_6$ haloalkylidene, phenyl or phenyl optionally substituted by one to three substituents independently selected from halogen and trihalomethylthio;
comprising providing a compound of formula IX:

(IX)

wherein $R^1$ is $C_1$-$C_4$haloalkyl and $R^3$ is methyl or ethyl;
according to the processes described above; and
reacting the compound of formula IX or the corresponding acid-halide with a compound of formula XI:

$H_2N$-A-B-D (XI)

wherein A, B and D are as defined for the compound of formula X.

The compound of formula X is preferably a compound of formula XII (Isopyrazam), a compound of formula XIII (Sedaxane), a compound of formula XIV, a compound of formula XV (Penthiopyrad), a compound of formula XVI (Bixafen), a compound of formula XVII (Fluxapyroxad), a compound of formula XVIII, or a compound of formula XIX:

(XII)

(XIII)

(XIV)

(XV)

(XVI)

(XVII)

(XVIII)

(XIX)

The step of reacting the compound of formula IX or the corresponding acid-halide with a compound of formula XI may be performed according to known methods, e.g. as described in WO 2004/035589 or WO 2009/135860. For example, the compound of formula IX may be treated with a halogenating agent, such as thionyl chloride, oxalyl chloride, phosgene, $SF_4$, DAST, deoxofluor or thionylbromide to provide the acid-halogen, e.g. the acid chloride, which may then be reacted with the compound of formula XI in the presence of a suitable base, e.g. LiOH, KOH, NaOH, $NEt_3$, $NaHCO_3$, $KHCO_3$, $Na_2CO_3$ or $K_2CO_3$, e.g. in a solvent such as toluene, xylenes, dichloromethane, ethyl acetate or DMF, e.g. at $-10°$ C. to $30°$ C.

Isopyrazam, Sedaxane, Penthiopyrad, Fluxapyroxad and Bixafen are known fungicides. The compound of formula XIV is known, e.g. from WO 2007/048556, the compound of formula XVIII is known e.g. from WO 2010/000612, the compound of formula XIX is known e.g. from WO 2008/053044.

We have found that the compounds of formula I and IV have different boiling points which may be exploited to separate the compound of formula I from the compound of formula IV. Thus, the process may comprise separating a mixture of compounds of formula I and IV by distillation. For example, iso-DFPE has a boiling point of approximately 95° C./10 mbar, whereas DFPE has a boiling point of approximately 120° C./1 mbar. This separation step may be performed after completion of isomerisation or may be performed simultaneously with isomerisation, e.g. when the process is continuous.

In a further aspect of the invention there is provided a method of separating a compound of formula IV (IV)

wherein $R^1$ is $C_1$-$C_4$ haloalkyl, $R^2$ is $C_1$-$C_6$ alkyl and $R^3$ is methyl or ethyl;

from a compound of formula I (I)

wherein wherein $R^1$ is $C_1$-$C_4$ haloalkyl, $R^2$ is $C_1$-$C_6$ alkyl and $R^3$ is methyl or ethyl;

by distillation.

The compound of formula I may be purified by crystallisation.

Preferably the identity of substituents $R^1$, $R^2$ and $R^3$ is the same for the compound of formula I and IV. Preferred definitions of $R^1$, $R^2$, and $R^3$ are the same as those given above. Most preferably $R^1$ is difluoromethyl, $R^2$ is $C_1$-$C_6$ alkyl e.g. ethyl and $R^3$ is methyl. Preferably for both the compound of formula I and the compound of formula IV $R^1$ is difluoromethyl, $R^2$ is ethyl and $R^3$ is methyl. In another embodiment for both the compound of formula I and the compound of formula IV $R^1$ is trifluoromethyl, $R^2$ is ethyl and $R^3$ is methyl. Preferably the distillation is vacuum distillation.

Table 1 shows examples of compounds of formula I of the invention.

TABLE 1

Compounds of formula I (I)

| Comp. No. | $R_1$ | $R_2$ | $R_3$ |
|---|---|---|---|
| A1 | $CF_2H$ | $CH_2CH_3$ | $CH_3$ |
| A2 | $CF_2H$ | $CH_3$ | $CH_3$ |
| A3 | $CF_2H$ | $CH_3$ | $CH_2CH_3$ |
| A4 | $CF_2H$ | $CH_2CH_3$ | $CH_2CH_3$ |
| A5 | $CF_3$ | $CH_2CH_3$ | $CH_3$ |
| A6 | $CF_3$ | $CH_3$ | $CH_3$ |
| A7 | $CF_3$ | $CH_3$ | $CH_2CH_3$ |
| A8 | $CF_3$ | $CH_2CH_3$ | $CH_2CH_3$ |

The present invention will now be described by way of the following non-limiting Examples. Those skilled in the art will promptly recognize appropriate variations from the procedures both as to reactants and as to reaction conditions and techniques.

All references mentioned herein are incorporated by reference in their entirety. All aspects and preferred features of the invention may be combined with each other, except where this is evidently not possible.

FIGURES

FIG. 1

FIG. 2

FIG. 2 shows the effect of temperature on the rate of isomerisation. The Y axis indicates the amount of conversion of iso-DFPE to DFPE. The X axis indicates time. Triangles correspond to 165° C., squares to 156° C. and diamonds to 148° C. Experimental details are described under Example 6.

FIG. 3

FIG. 3 shows the effect of acid concentration on the rate of isomerisation The Y axis indicates the amount of conversion of the iso-DFPE to DFPE. The X axis indicates time. Experimental details are described under Example 7.

FIG. 4

FIG. 5

FIG. 6

EXAMPLES

Example 1

Ethyl 3-(difluoromethyl)-1-methyl-1H-pyrazole-4-carboxylate (DFPE): To 20.4 g of ethyl 5-(difluoromethyl)-1-methyl-1H-pyrazole-4-carboxylate (iso-DFPE) was added 14.4 g of trimethyl phosphate and 0.82 g of methane sulfonic acid. The mixture was heated to 170° C. and stirred for 7 hours. The solution was cooled and distilled to recover recycled trimethyl phosphate and 2.0 g of starting ethyl 5-(difluoromethyl)-1-methyl-1H-pyrazole-4-carboxylate. The remaining solution was added to 50 g of cold water. The solution was allowed to stir for 30 min. The precipitating solid was filtered and dried to give 16.2 g of product.

Example 2

Ethyl 3-(difluoromethyl)-1-methyl-1H-pyrazole-4-carboxylate (DFPE): To 20.4 g of ethyl 5-(difluoromethyl)-1-methyl-1H-pyrazole-4-carboxylate (iso-DFPE) was added 11.3 g of dimethyl phosphite and 0.82 g of methane sulfonic acid. The mixture was heated to 170° C. and stirred for 7 hours. The solution was cooled and distilled to recover recycled trimethyl phosphate and 0.9 g of starting ethyl 5-(difluoromethyl)-1-methyl-1H-pyrazole-4-carboxylate (iso-DFPE). The remaining solution was added to 50 g of cold water. The solution was allowed to stir for 30 min. The precipitating solid was filtered and dried to give 14.1 g of product.

Example 3

To 20.4 g of ethyl 5-(difluoromethyl)-1-methyl-1H-pyrazole-4-carboxylate (iso-DFPE), was added 2.8 g of trimethylphosphate and 0.4 g of methane sulfonic acid. The mixture was heated gradually to 180° C. and held for 8 hours to give a ratio of ethyl 3-(difluoromethyl)-1-methyl-1H-pyrazole-4-carboxylate (DFPE):iso-DFPE of 94:6. The unreacted iso-DFPE was then distilled off at 90° C./10 mbar and then recycled in the next batch. The crude product of DFPE (mp ~75° C., bp ~120° C./1 mbar) from the distillation bottom was dissolved in toluene and washed with water to remove ionic by-products. The resulting solution of crude ethyl 3-(difluoromethyl)-1-methyl-1H-pyrazole-4-carboxylate (DFPE) can be used directly for the next step, e.g. hydrolysis, without any further purification. The combined chemical yield from the isomerization reaction for both DFPE and iso-DFPE is 94.1%.

Example 4

This Example shows that the isoform of ethyl 5-(difluoromethyl)-1-methyl-1H-pyrazole-4-carboxylate (iso-DFPE) reverts into the alternative N-alkylated isomer in the presence of acid.

Figure 1:
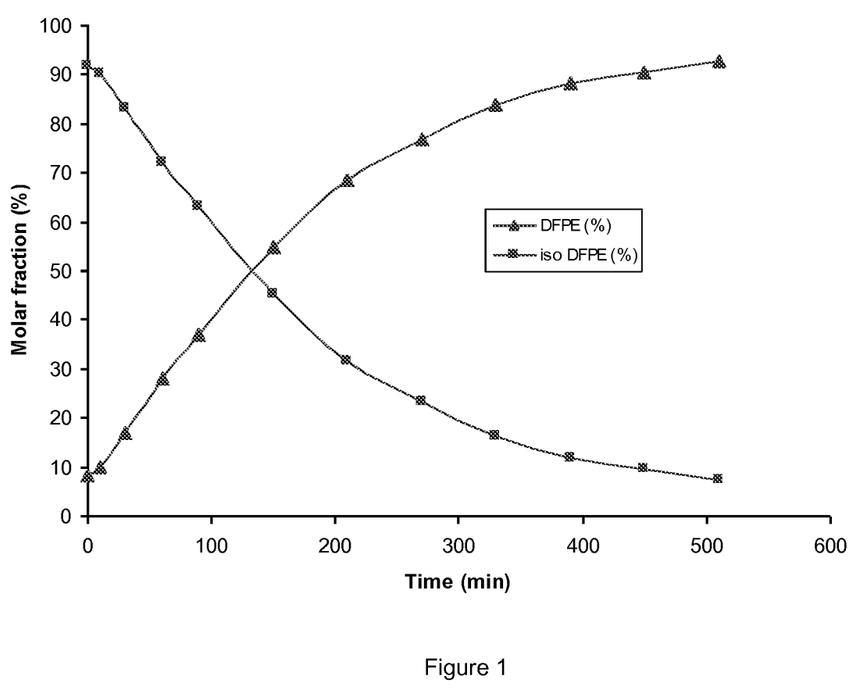
FIG. 1 shows that ethyl 5-(difluoromethyl)-1-methyl-1H-pyrazole-4-carboxylate (iso-DFPE) reverts into ethyl 3-(difluoromethyl)-1-methyl-1H-pyrazole-4-carboxylate (DFPE) in the presence of acid. The Y axis indicates the ratio of the isomers. The X axis indicates time. Squares correspond to iso-DFPE, whereas triangles correspond to DFPE. Experimental details are described under Example 4.

To 4.1 g of iso-DFPE was added 8.2 g of trimethyl phosphate and 0.30 g of polyphosphoric acid. The mixture was heated to 170° C. and stirred for 8 hours. Samples were taken periodically for GC analysis. Results are shown in FIG. 1.

Example 5

The following experiment provides evidence that an equilibrium exists between ethyl 3-(difluoromethyl)-1-methyl-1H-pyrazole-4-carboxylate (DFPE) and ethyl 5-(difluoromethyl)-1-methyl-1H-pyrazole-4-carboxylate (iso-DFPE) in the presence of acid.

To 4.0 g DFPE was added 10.0 g of trimethyl phosphate and 0.30 g of polyphosphoric acid. The mixture was heated to 170° C. and stirred for 5 hours. Samples were taken periodically for GC analysis. The results are shown in Table 2.

TABLE 2

| Time (min) | DFPE fraction (%) | Iso-DFPE fraction (%) |
| --- | --- | --- |
| 0 | 100.0 | Not detected |
| 90 | 97.2 | 2.8 |
| 180 | 95.4 | 4.6 |
| 300 | 95.4 | 4.6 |

Example 6

Figure 2:
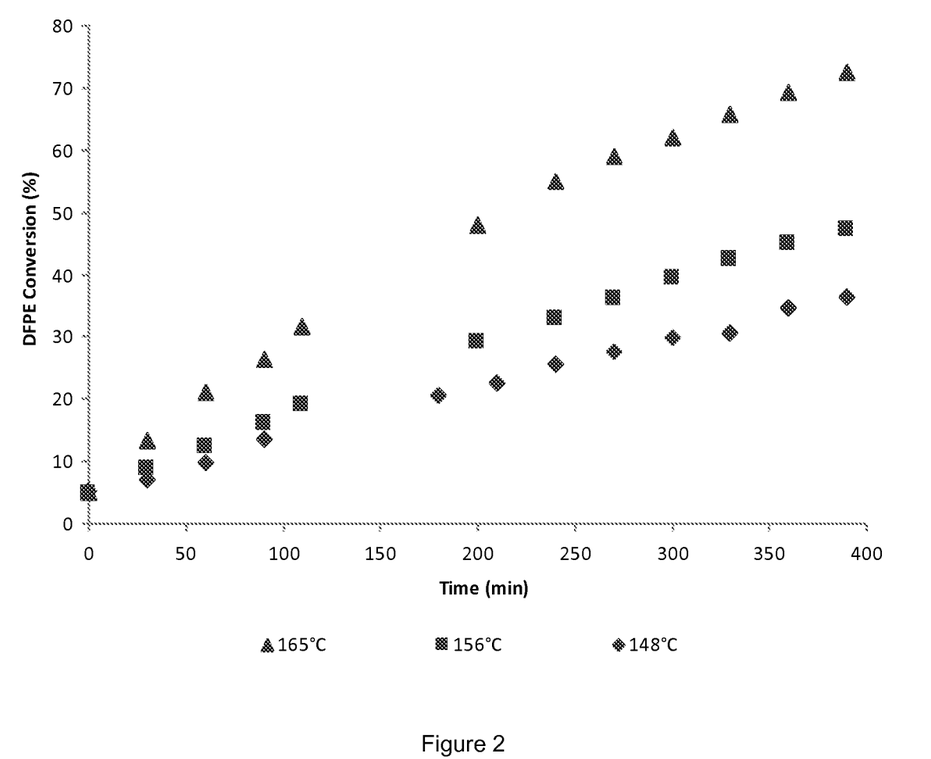

To 6.0 g of ethyl 5-(difluoromethyl)-1-methyl-1H-pyrazole-4-carboxylate (iso-DFPE) was added 12.0 g of trimethyl phosphate and 0.45 g of polyphosphoric acid. The mixture was heated to the desired temperature and stirred for 6-7 hours. Samples were taken periodically for GC analysis. Results are shown in FIG. 2.

Example 7

Figure 3:
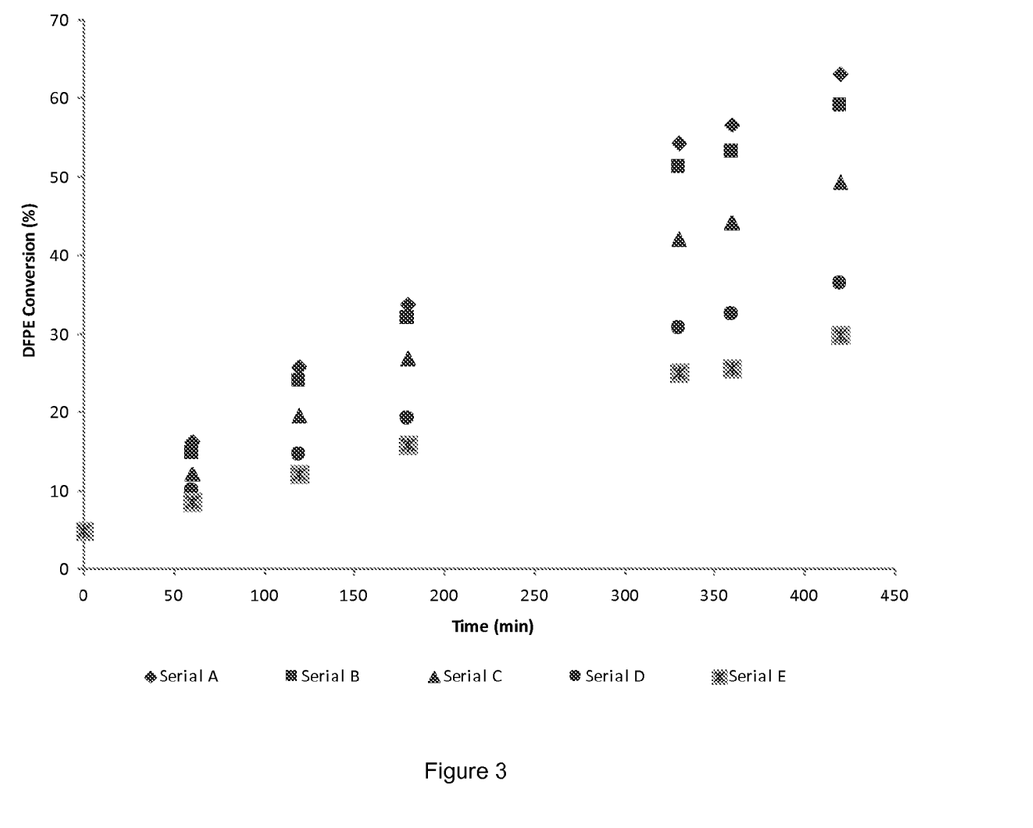

In each reactor of a multi-pot reaction block was placed ethyl 5-(difluoromethyl)-1-methyl-1H-pyrazole-4-carboxylate (iso-DFPE), trimethyl phosphate and polyphosphoric acid. The reaction block was heated to 156° C. and held for 7 hours. Samples were taken from each reactor periodically for GC analysis. Table 3 describes conditions of 5 experiments in this series.

TABLE 3

| Experimental serial | Iso-DFPE (g) | TMP (g) | PPA (g) |
|---|---|---|---|
| A | 3.0 | 6.0 | 0.44 |
| B | 3.0 | 3.0 | 0.22 |
| C | 3.0 | 6.0 | 0.22 |
| D | 3.0 | 12.0 | 0.22 |
| E | 3.0 | 6.0 | 0.11 |

Results are shown in FIG. 3.

Example 8

Figure 4A:
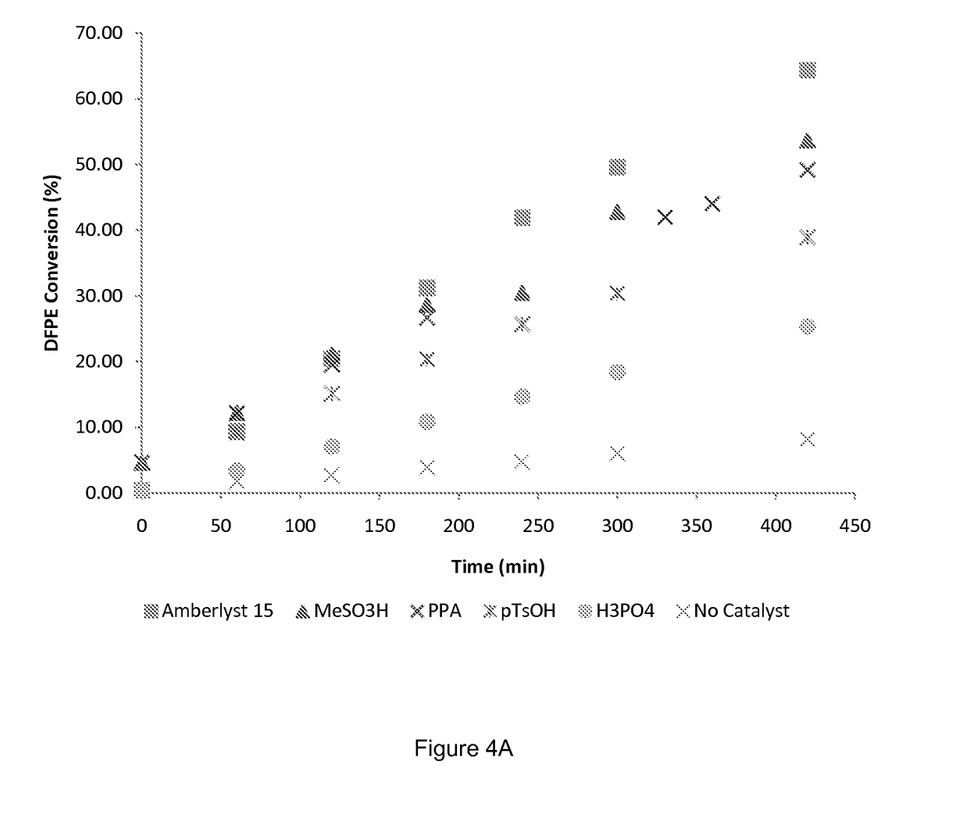
FIGS. 4A and 4B shows the effect of different acids on the rate of isomerisation. The Y axis indicates the amount of conversion of the iso-DFPE to DFPE. Experimental details are described under Example 8. (PPA=polyphosphoric acid, pTsOH=p-toluenesuphonic acid, DMS=dimethylsulphate, THF=tetrahydrofuran.)
Figure 4B:
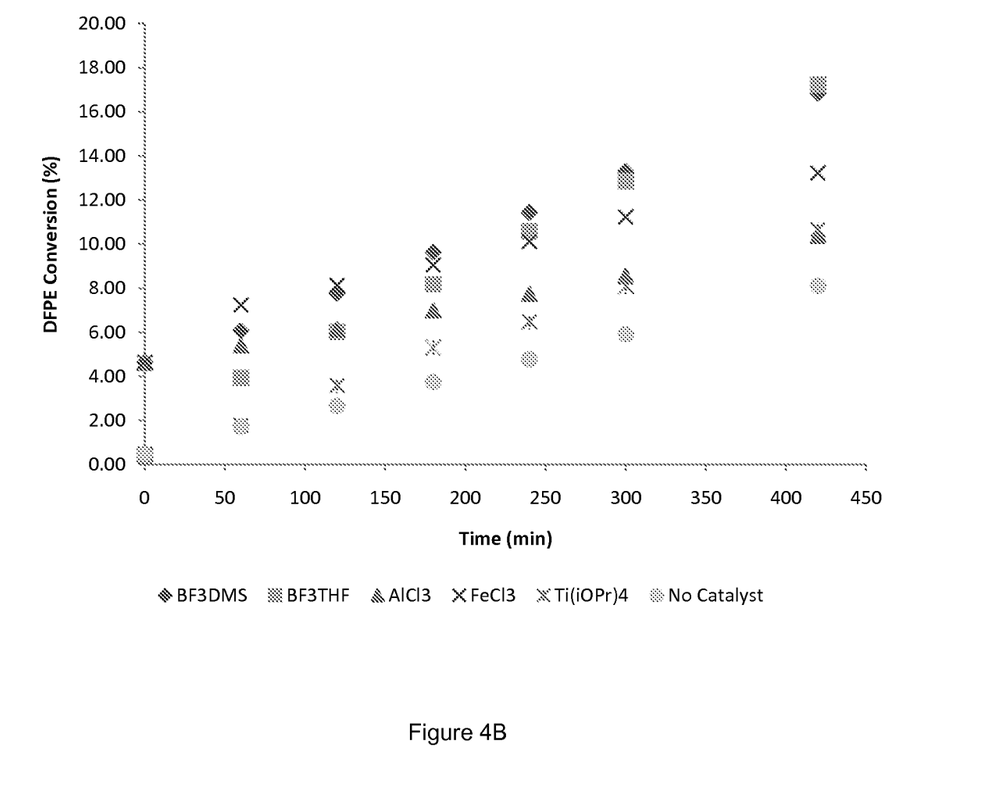

In each reactor of a multi-pot reaction block was placed 3.0 g of ethyl 5-(difluoromethyl)-1-methyl-1H-pyrazole-4-carboxylate (iso-DPFE), 6.0 g of trimethyl phosphate, and the selected catalyst (0.65 mmol, except Amberlyst® 15: 1.0 g). The reaction block was heated to 156° C. and stirred for 7 hours. Samples were taken periodically for GC analysis. Results are shown in FIGS. 4A and 4B.

Example 9

Figure 5:
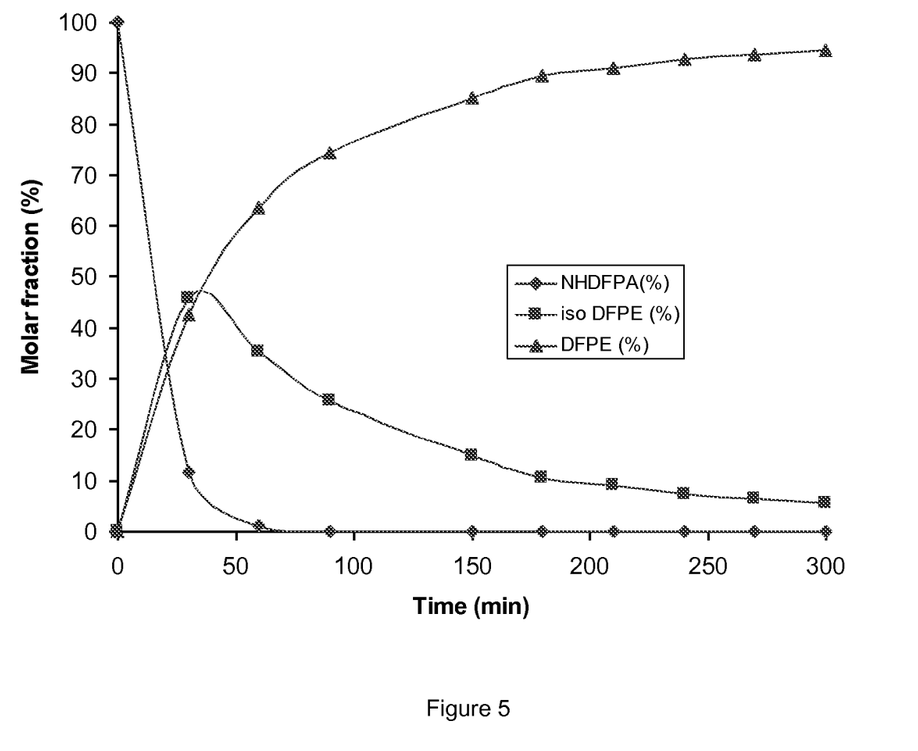
FIG. 5 shows a reaction profile for the synthesis of DFPE from ethyl 3-difluoromethylpyrazole-4-carboxylate (NHDFPE), trimethyl phosphate and 0.60 g of polyphosphoric acid and the simultaneous isomerisation of the iso-DPFE to the desired DFPE. The Y axis indicates mole fraction. The X axis indicates time. Diamonds correspond to ethyl 3-d ifluoromethylpyrazole-4-carboxylate (NHDFPE), squares correspond to iso-DFPE, triangles correspond to DFPE. Experimental details are described under Example 9.

To 8.2 g of ethyl 3-difluoromethylpyrazole-4-carboxylate (NHDFPE) was added 24.6 g of trimethyl phosphate and 0.60 g of polyphosphoric acid. The mixture was heated to 170° C. and stirred for 5 hours. Samples were taken periodically for GC analysis. The results are shown in FIG. 5.

Example 10

Figure 6:
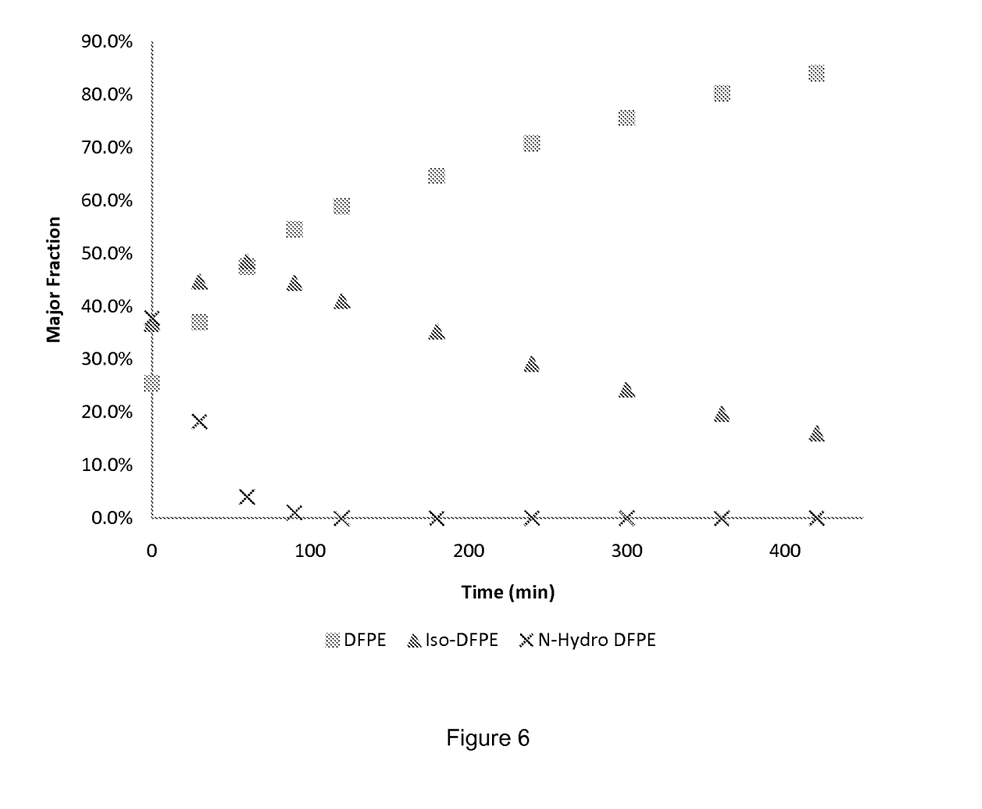
FIG. 6 shows a reaction profile for the synthesis of DFPE from ethyl 3-difluoromethylpyrazole-4-carboxylate (NHDFPE) using dimethyl methylphosphonate and methanesulfonic acid and the simultaneous isomerisation of the iso-DPFE to the desired DFPE. The Y axis indicates mole fraction. The X axis indicates time. Crosses correspond to ethyl 3-difluoromethylpyrazole-4-carboxylate (NHDFPE), triangles correspond to iso-DFPE, squares correspond to DFPE. Experimental details are described under Example 10.

To 23.2 g of ethyl 3-difluoromethylpyrazole-4-carboxylate (NHDFPE) was added 19.2 g of dimethyl methyl phosphonate and 0.48 g of methanesulfonic acid. The mixture was heated to 160° C. and stirred for 7 hours. Samples were taken periodically for GC analysis. The results are shown in FIG. 6.

Example 11

To 21.66 g of 3-difluoromethylpyrazole-4-carboxylate (NHDFPE) was added 25.3 g of trimethyl phosphite and 0.48 g of methanesulfonic acid. The mixture was heated to 160° C. in a Parr reactor and stirred for 7 hours. A sample was taken at the end of the 7 hour period and analysed by GC. GC analysis indicated 63.7% DFPE and 30.8% iso-DFPE.

Example 12

To 69.6 g of 85% pure ethyl 5-(difluoromethyl)-1-methyl-1H-pyrazole-4-carboxylate (iso-DFPE):ethyl 3-(difluoromethyl)-1-methyl-1H-pyrazole-4-carboxylate (DFPE) (35:65), additionally containing 2-4 mol % methyl sulphuric acid, was added 4.2 g of trimethylphosphate. The mixture was heated to 180° C. for 6 hours to give a ratio of 10:90 Iso-DFPE:DFPE. The unreacted iso-DFPE was then distilled out and recycled in the next batch. The crude product of DFPE from distillation bottom was dissolved in toluene and can be used directly for the next step, e.g. hydrolysis, without any further purification. The combined yield from the isomerization reaction for both DFPE and iso DFPE is 92.5%.

What is claimed is:

1. A process for the preparation of a compound of formula I:

(I)

wherein $R^1$ is $C_1$-$C_4$ haloalkyl;
$R^2$ is optionally substituted alkyl, optionally substituted aryl or optionally substituted heteroaryl; and
$R^3$ is methyl or ethyl;
comprising reacting a compound of formula IV:

(IV)

wherein $R^1$, $R^2$ and $R^3$ are as defined for the compound of formula I;
with a compound of formula III or IIIA:

(III)

(IIIA)

wherein n is 0 or 1;
$R^3$ is as defined for the compound of formula I;
$R^4$ is hydrogen, optionally substituted alkyl, optionally substituted aryl or optionally substituted heteroaryl;
in the presence of an acid.

2. A process according to claim 1, wherein the process is for increasing the proportion of a compound of formula I in a mixture comprising a compound of formula I and a compound of formula IV.

3. A process for the preparation of a compound of formula I:

wherein $R^1$ is $C_1$-$C_4$ haloalkyl;
$R^2$ is optionally substituted alkyl, optionally substituted aryl or optionally substituted heteroaryl; and
$R^3$ is methyl or ethyl;
comprising reacting a compound of formula II:

wherein $R^1$ and $R^2$ are as defined for the compound of formula I;
with a compound of formula III or IIIA:

wherein n is 0 or 1;
$R^3$ is as defined for the compound of formula I;
$R^4$ is hydrogen, optionally substituted alkyl, optionally substituted aryl or optionally substituted heteroaryl;
in the presence of an acid.

4. A process according to claim 1, wherein the acid is an acid other than one formed in situ from a compound of formula III or IIIA.

5. A process according to claim 1, wherein the acid is an exogenous acid.

6. A process for inter-converting a compound of formula IV and a compound of formula I according to Scheme I:

Scheme I wherein $R^1$ is $C_1$-$C_4$ haloalkyl;
$R^2$ is optionally substituted alkyl, optionally substituted aryl or optionally substituted heteroaryl; and
$R^3$ is methyl or ethyl;
using a compound of formula III or IIIA:

wherein n is 0 or 1; $R^3$ is as defined for the compound of formula I and IV; and
$R^4$ is hydrogen, optionally substituted alkyl, optionally substituted aryl or optionally substituted heteroaryl;
and an acid as inter-conversion reagents.

7. A process according to claim 1, wherein the acid is provided in a catalytic amount.

8. A process according to claim 1, wherein the acid is a sulphonic acid, a phosphoric acid, a phosphonic acid, a boronic acid, a borane, a haloboron, a titanium IV salt, a silicon oxide or an aluminium oxide.

9. A process according to claim 1, wherein the acid is a phosphoric acid, a phosphonic acid or a sulphonic acid.

10. A process according to claim 1, wherein the compound of formula III or IIIA is dimethyl methyl phosphonate, trimethyl phosphite, trimethyl phosphate or dimethyl phosphite.

11. A process according to claim 1, wherein the compound of formula III or IIIA is provided in less than an equimolar amount compared to the molar amount of the compound of formula IV or the combined molar amount of compounds of formula IV and I when both are present.

12. A process according to claim 1, wherein the process is for preparing a compound of formula VI:

comprising reacting a compound of formula VII:

(VII)

with a compound of formula VIII:

(VIII)

in the presence of a phosphoric acid, a phosphonic acid or a sulphonic acid.

13. A process according to claim 1 wherein
n is 1;
$R^1$ is difluoromethyl or trifluoromethyl;
$R^2$ is $C_1$-$C_6$ alkyl;
$R^3$ is methyl; and
$R^4$ is hydrogen or $C_1$-$C_6$ alkyl.

* * * * *